United States Patent [19]
Hunt et al.

[11] Patent Number: 5,933,809
[45] Date of Patent: Aug. 3, 1999

[54] COMPUTER SOFTWARE FOR PROCESSING MEDICAL BILLING RECORD INFORMATION

[75] Inventors: William A. Hunt; Elizabeth F. Yauch; Mark Denovich, all of Pittsburgh, Pa.

[73] Assignee: Medcom Solutions, Inc., Pittsburgh, Pa.

[21] Appl. No.: 08/608,730

[22] Filed: Feb. 29, 1996

[51] Int. Cl.$^6$ .................................................. G06F 159/00
[52] U.S. Cl. ................................................... 705/3; 705/2
[58] Field of Search ................................. 705/2, 3, 4, 17; 395/200.15

[56] References Cited

U.S. PATENT DOCUMENTS 4,858,121  8/1989  Barber et al. ............................... 705/1

OTHER PUBLICATIONS

Scahner, "Software cracks miscoded claims: computer helps cut waste in health costs . . . ", Business Insurance, v26, n19, p21(1), May 11, 1992, Dialog file 148, Accession No. 05661345.

Klingman et al., "Outcomes of surgery under Medicaid", Health Care Financing Review, v11, n3, p1(16), Sep. 1990, Dialog file 149, Accession No. 01241720.

Wade et al., "Computer Use Can Increase Practice Productivity, Profitability", Ophthalmology Times, Nov. 1, 1993, pf. 108, Dialog file 16, Accession No. 04688496.

*Primary Examiner*—Frantzy Poinvil
*Attorney, Agent, or Firm*—Titus & McConomy LLP

[57] ABSTRACT

A computer-coded software instructions capable of being executed by a conventional computer microprocessor to perform information processing on pre-existing medical billing record information, preferably consisting of hospital or individual doctor Medicare billing records. The software contains at least one set of instructions for receiving, converting, sorting and storing input information from the pre-existing medical billing records into a form suitable for processing. The software contains at least one set of instructions for processing the input medical billing record information, preferably to identify potential Medicare "72 hour billing rule" violations. This processing is preferably performed by comparing each input medical billing record containing dates of medical inpatient admission and discharge to each input medical billing record containing a date of medical outpatient service. The inpatient and outpatient billing records are first compared to determine if they contain matching patient identification codes to identify all the records originating from the same patient. If matching patient identification codes are found the inpatient and outpatient billing records are further compared to determine if the date of outpatient service fell within a preselected time period, preferably 72 hours, prior to the date of inpatient admission. If so, the matching inpatient and outpatient billing records are distinguished and stored separately for further processing. If not, the matching inpatient and outpatient billing records are compared to determine if the date of outpatient service fell between the inpatient admission and discharge dates. If this is the case, the matching inpatient and outpatient billing records are again distinguished and stored separately for further processing. If not, the program proceeds to the next set of billing records to repeat the sequence.

28 Claims, 3 Drawing Sheets

5,933,809

COMPUTER SOFTWARE FOR PROCESSING MEDICAL BILLING RECORD INFORMATION

FIELD OF THE INVENTION

The present invention relates to computer software designed for processing medical billing record information received from a pre-existing database, and in particular to processing medical billing record information to ensure compliance with the "72 hour billing rule" for submitting Medicare outpatient claims.

BACKGROUND OF THE INVENTION

The "72 hour billing rule" for submission of Medicare outpatient claims mandates that medical outpatient service performed within a 72 hour period prior to or during a "medically related" medical inpatient admission shall not be billed for outpatient reimbursement to Medicare. If an outpatient claim has been submitted and Medicare reimbursement has been received in either situation, the outpatient claim must be refunded to the payor of the claim. In some cases, the refund will be owed to the Medicare fund. In other cases, the refund will be owed to the provider of a coinsurance policy that supplements the Medicare coverage or to the patient as the payor of a deductible premium that covered the outpatient service. Finally, in some cases the refund will be owed to a combination of these payor sources if they all contributed to reimbursement of an erroneously billed outpatient claim.

Recently, several hospitals have been the subject of a U.S. Department of Justice investigation into fraudulent Medicare billing practices. It was found that some hospitals have been disregarding the "72 hour billing rule" by improperly submitting claims for Medicare reimbursement of outpatient service that are prohibited under the rule. As a result the Justice Department has entered into a settlement with some of the offending hospitals to ensure that the erroneously billed outpatient claims are properly accounted for and refunded, and to ensure that a compliance mechanism is in place to prevent future erroneous outpatient billings.

To ensure compliance with the Justice Department settlement agreement, a need has arisen for a computer software program to screen pre-existing paid Medicare billing records to determine what billing records could have potentially violated the "72 hour billing rule". Due to the enormous volume of pre-existing billing records which must be screened, it is imperative that this software be able to interpret data from existing billing records automatically without any need for manual input of the data. The software must also have the capability to automatically segregate and separately store the records where potential violations could exist for further examination to determine whether the rule has actually been violated in those cases. Finally, the software must have the capability for updating the records where violations have occurred in order to track the refund process to completion.

The present invention satisfies the needs outlined above by providing a software package that will automatically screen pre-existing medical billing record databases to identify potential violations of the "72 hour billing rule". The software will automatically convert pre-existing Medicare billing record information into a form suitable for identifying the potential violations. It will automatically segregate and separately store the billing records which potentially violate the rule for further processing to determine if violations have occurred. Finally, it provides the capability for updating records of actual violations to document the payment of refunds to the proper parties.

Although the software was initially developed for use in conjunction with the Medicare "72 hour billing rule", the rapidly escalating and changing demands of medical service providers with respect to the processing of medical billing information dictated that the software be designed with the flexibility for adaptation to different medical billing record applications. One such application is the identification of billing records for patients transferred between medical service providers during treatment of the same or related medical problems. Thus it is anticipated that the existing capabilities of the software will allow its future use in a wide variety of medical billing applications other than the Medicare "72 hour billing rule".

Accordingly, it is an object of the present invention to provide a computer software program to automatically screen pre-existing medical billing record information.

It is further object of the present invention to provide a computer software program to automatically screen pre-existing medical billing record information to identify potential violations of the Medicare "72 hour billing rule".

It is a further object of the present invention to provide a computer software program to automatically convert pre-existing Medicare billing record information into a form suitable for identifying potential Medicare "72 hour billing rule" violations.

It is a further object of the present invention to provide a computer software program to automatically segregate and separately store the billing records which potentially violate the Medicare "72 hour billing rule" for further processing to determine if violations have occurred.

It is a further object of the present invention to provide a computer software program with the capability for updating records of actual Medicare "72 hour billing rule" violations to document the payment of refunds to the proper parties.

It is a further object of the present invention to automatically screen pre-existing medical billing record information to identify patients transferred between medical service providers during treatment of the same or related medical problems.

SUMMARY OF THE INVENTION

The preferred embodiment of the invention consists of computer-coded software instructions capable of being executed by a conventional computer microprocessor to perform information processing on pre-existing medical billing record information, preferably consisting of hospital or individual doctor Medicare billing records. The software contains at least one set of instructions for receiving, converting, sorting and storing input information from the pre-existing medical billing records into a form suitable for processing.

The software contains at least one set of instructions for processing tie input medical billing record information, preferably to identify potential Medicare "72 hour billing rule" violations. This processing is preferably performed by comparing each input medical billing record containing dates of medical inpatient admission and discharge to each input medical billing record containing a date of medical outpatient service. The inpatient and outpatient billing records are first compared to determine if they contain matching patient identification codes to identify all the records originating from the same patient. If matching patient identification codes are found the inpatient and outpatient billing records are further compared to determine if the date of outpatient service fell within a preselected time period, preferably 72 hours, prior to the date of inpatient admission. If so, the matching inpatient and outpatient billing records are distinguished and stored separately for further processing. If not, the matching inpatient and outpatient billing records are compared to determine if the date of outpatient service fell between the inpatient admission and discharge dates. If this is the case, the matching inpatient and outpatient billing records are again distinguished and stored separately for further processing. If not, the program proceeds to the next set of billing records to repeat the sequence.

The software contains a set of instructions for updating the matching medical billing record information to determine if the inpatient admission was "medically related" to the outpatient service, and to indicate the payees and amounts of refunds generated for erroneously billed outpatient service. The software also contains a set of instructions for displaying the information contained in the processed medical billing records in either visual or printed form, and a set of instructions for storing chronological information uniquely identifying each user of the software and the corresponding time of use of the software for audit purposes.

An alternative embodiment of the invention performs all of the tasks of the preferred embodiment, substituting a processing sequence in which Medicare claims will be distinguished for future examination and possible reimbursement for inpatient admissions that fell on the same date as an inpatient discharge from another medical treatment provider facility.

BRIEF DESCRIPTION OF THE DRAWINGS

FIG. (1) is a block diagram of the preferred embodiment of the data processing system used to implement the preferred embodiment of the medical billing record processing software of the present invention.

FIG. (2) is a flow diagram outlining the functioning of the preferred embodiment of the medical billing information processing software of the present invention.

Figure 1:
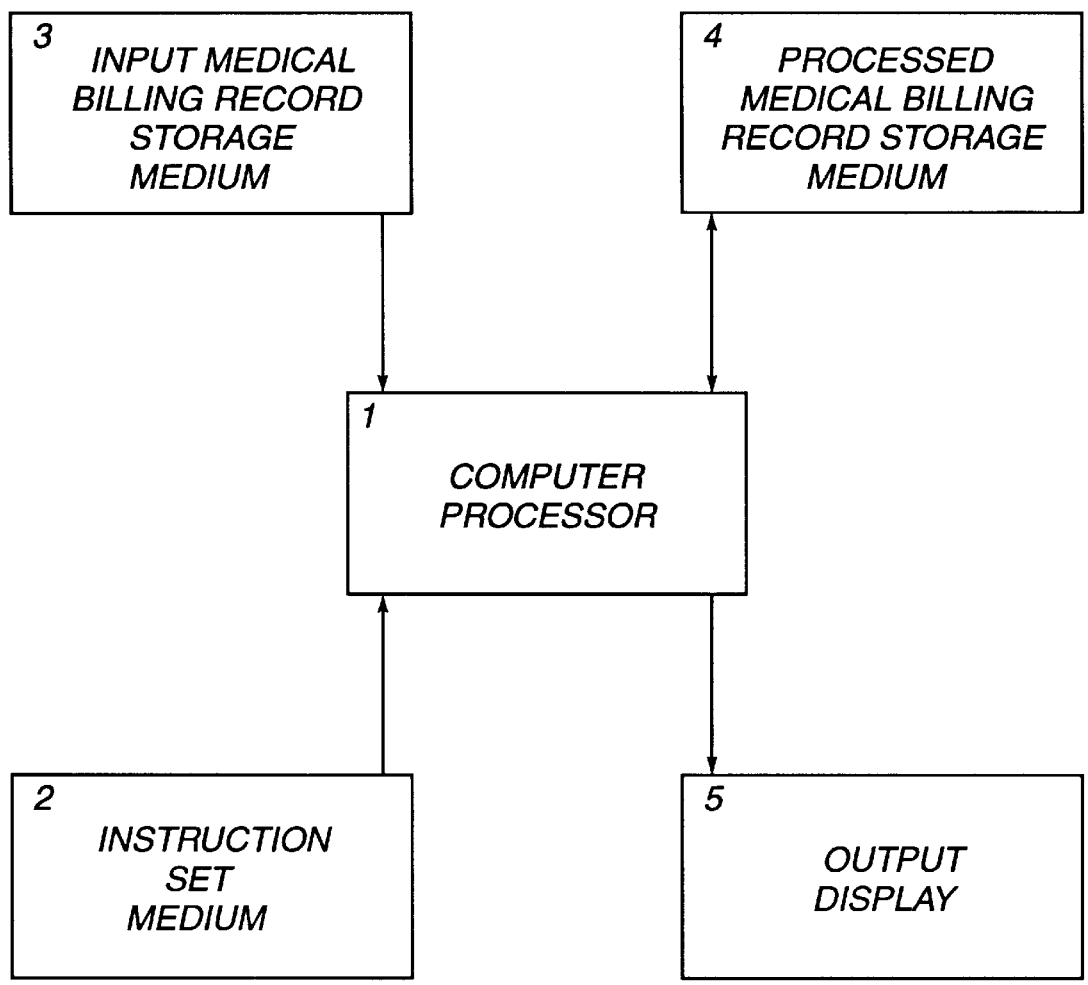
Figure 2:
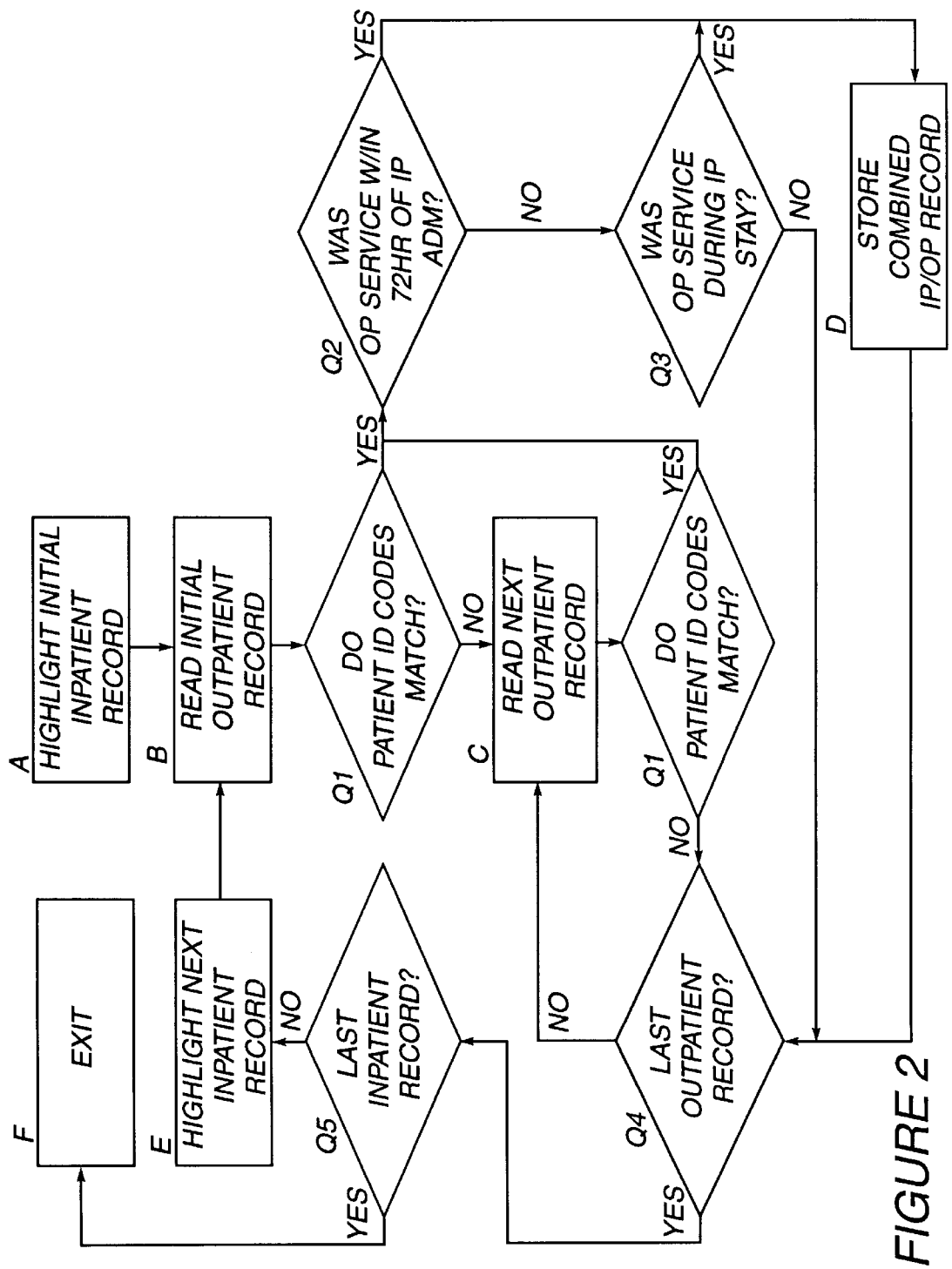
Figure 3:
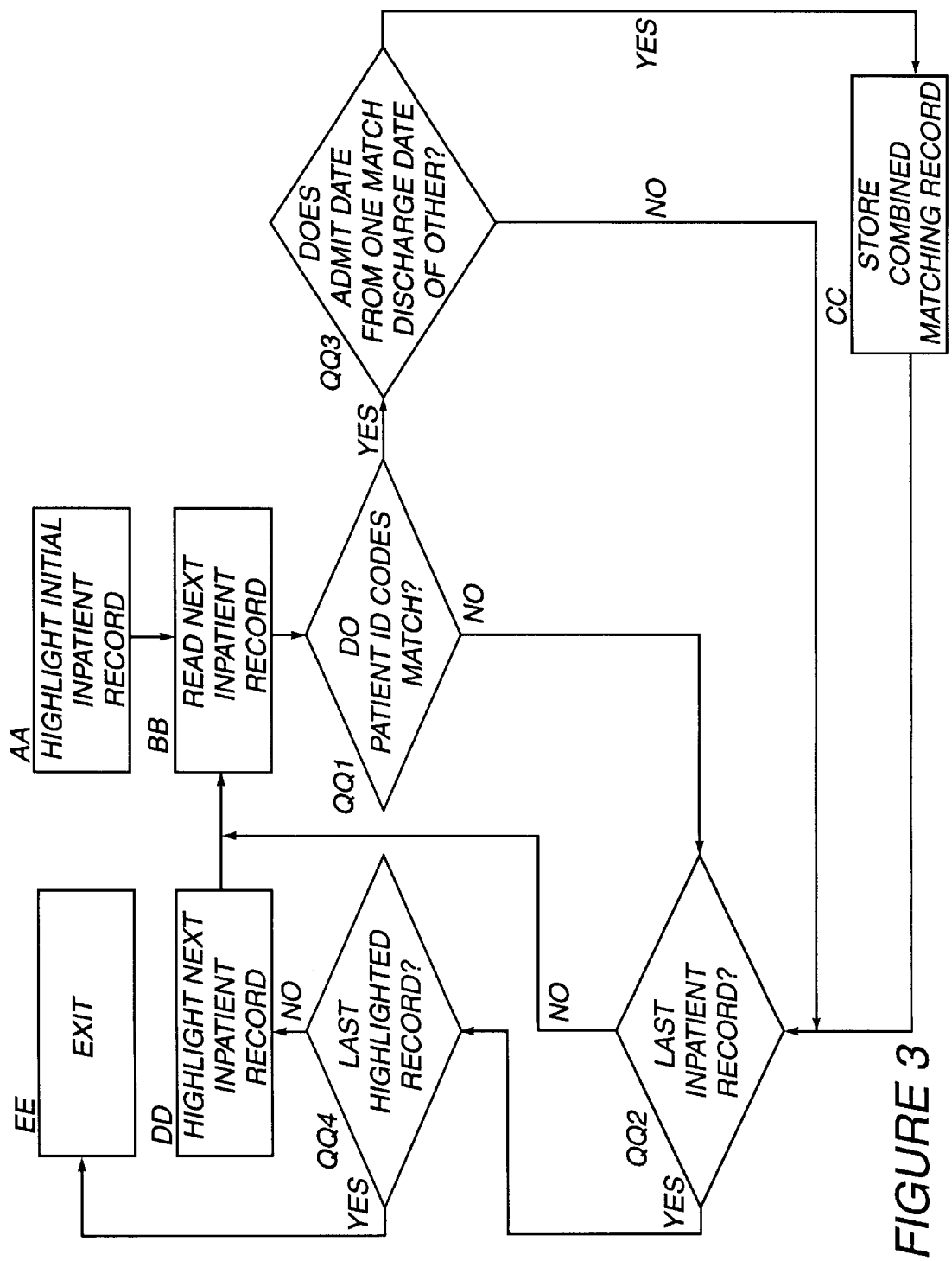

FIG. (3) is a flow diagram outlining the functioning of a second embodiment of the medical billing information processing software of the present invention.

DETAILED DESCRIPTION OF THE PREFERRED EMBODIMENT

FIG. (1) provides a block diagram of the preferred embodiment of the data processing system used to implement the medical billing record processing software. The system is driven by a computer processor 1 which can be implemented by any conventional microprocessor currently available on the market including the Intel Corporation 80X86 series processors and the Motorola Corporation 68000 series processors.

The computer processor 1 interfaces with at least three computer-readable storage mediums 2, 3 and 4 to process the medical billing record data in accordance with the software instructions. These computer-readable storage mediums can be implemented on the same or on separate storage devices. The storage devices can be implemented in the form of stand-alone devices such as personal computer (PC) magnetic storage hard disk drives, magnetic portable floppy disks and optical storage compact disks (CDs), or the information contained on the storage mediums can be retrieved by the computer processor 1 from networked storage devices such as Local Area Network (LAN) file servers or Internet bulletin board address sites.

At least one computer-readable storage medium 2 contains the programmed software instructions which direct processing of the medical billing information in accordance with the present invention as dictated by the processing steps in FIGS. (2) and (3). These computer-coded software instructions can be written and in any high level programming language such as Visual BASIC, PASCAL or the "C" languages including fourth generation (4GL) or object-oriented programming languages. These high-level language source code instructions are retrieved from the instruction set storage medium 2 and compiled for the operating system of the computer processor 1 into object code assembly language and machine language for storage on the instruction set storage medium 2 and subsequent execution.

At least one other computer-readable storage medium 3 contains the input medical billing information to be processed by the software. This input medical billing information is preferably stored in a pre-existing database on the input medical billing record storage medium 3 in any universally computer-readable format such as American Standard Code for Information Interchange (ASCII) text, EBCIDIC, dBase, FoxPro, Lotus or Microsoft Excel or ACCESS, that can be converted into a form suitable for processing by the software.

After the input medical billing information has been obtained by the computer processor 1 from the input medical billing record storage medium 3 and converted into a form suitable for use by the processing software, it is stored in a processed medical billing record storage medium 4 for future processing in accordance with the program steps in FIG. (2). The processed medical billing record storage medium 4 contains at least three separate databases: a first database for medical inpatient billing records; a second database for medical outpatient billing records; and a third "exceptions" database for combining matching inpatient and outpatient billing records as described more fully below.

The information stored in the processed medical billing record storage medium 4 can be processed by the computer processor 1 for use by an output display device 5. This output display 5 device can display the information in visual form by directing the output to a viewing screen such as conventional cathode ray tube (CRT) screen or the information can be displayed in printed form by directing the output to a conventional computer printer such as a dot matrix or laser printer.

PROGRAM OPERATION

Before processing the medical billing record data to determine if a potential violation of the Medicare "72 hour billing rule" has occurred, the computer processor 1 reads all Medicare Remittance Advice (RA) billing record information from a pre-existing database contained on the input medical billing record storage medium 3 for conversion into a format suitable for use by the processing software. After conversion the RA information is imported into the processed medical billing record storage medium 4 for future processing by the software. The actual conversion of the input billing record information into a form suitable for use by the processing software is accomplished by conversion instructions contained in the software of the present invention. The importing function can be performed by a database conversion program such as the "ACCESS" database conversion software manufactured by Microsoft Corporation or a similar database conversion software product, or by a customized database conversion program written specifically for this purpose.

The conversion and importing program instructions are provided in Appendix A. The conversion is accomplished as the conversion instructions receive and sort the input RA data from the input medical billing record storage medium 3. After conversion the RA data is then imported by the database conversion program into the processed medical billing record storage medium 4 where it is stored in the separate inpatient and outpatient billing record databases by inpatient or outpatient data type.

The input billing records are sorted by inpatient or outpatient data type by first examining the initial character of the individual data string representing each input billing record. If the initial character of the input data string is not a binary coded "1" it is a record that does not contain inpatient or outpatient data. The sorting program next searches for an ASCII-coded "A" or "B" in the input data string. If an "A" is found the input data string is stored in its own separate file in the inpatient billing record database. If a "B" is found the data string is stored in its own separate file in the outpatient billing record database. Each input billing record is sorted and stored only once such that each separate database on the processed medical billing record storage medium 4 contains a continuously up-to-date record of all input medical billing records processed by the software. This feature allows new input billing record information to be compared to billing record information previously processed and stored on the processed medical billing record storage medium 4.

Each input billing record is converted by breaking up the data string representing the billing record into individual segments of predetermined length that each correspond to a specific piece of information about the individual patient for whom the billing record was created, such as the patient's identification, the payment amount received or refunded by the medical service provider, the intermediary insurance or coinsurance provider, and any amounts of coinsurance or deductibles applicable to that individual patient for the service billed. The patient identification code is unique to each individual billed patient and can be the social security number of the individual patient or a Medicare insurance tracking number. The payment amount segment contains a separate hexadecimal coded character in its last byte for determining whether a payment was received by the medical service provider or refunded by the service provider to a receiving party. The hexadecimal coded letters "A" through "I" (which respectively represent the decimal digits 0 through 9) indicate that a payment was received by the medical service provider. The hexadecimal letters "J" through "R" (which again respectively represent the decimal digits 0 through 9) indicate that a payment was refunded by the medical service provider. A neighboring data string segment will indicate the receiving party of the refund. The software is programmed to look for each data string segment by its predetermined length and in the order the segment appears in the data string as it processes each input billing record for storage in the processed medical billing record storage medium 4. The preferred embodiment of the medical billing record processing software can function in accordance with the flow diagram shown in FIG. (2). A printout of the source code steps corresponding to the flow diagram steps of FIG. (2) is shown in Appendix B. The source code is written in the Visual BASIC programming language.

The processing instructions are loaded from the instruction set storage medium 2 into the computer processor 1 for execution after the importing operation described above is complete. In the first step A of the processing sequence the computer processor 1 reads and highlights the initial medical inpatient billing record contained in the processed medical billing record storage medium 4 for comparison with the initial medical outpatient billing record retrieved from the processed medical billing record storage medium 4 in processing step B.

As described above, each inpatient and outpatient medical billing record stored in the processed medical billing record storage medium 4 contains a patient identification code unique to a single billed medical patient. In processing step Q1 the computer processor 1 compares the patient identification codes from the inpatient and outpatient billing records retrieved in processing steps A and B, respectively, to determine whether a match exists. If not the computer processor 1 executes processing step C to retrieve the next outpatient billing record from the processed medical billing record storage medium 4, and then re-executes processing step Q1 to compare the patient identification code from the new outpatient billing record to the initial inpatient billing record highlighted in processing step A.

The computer processor 1 will repeat processing steps C and Q1 for each outpatient billing record that does not match the patient identification code contained in the initial inpatient billing record highlighted in processing step A. Prior to each repeat of processing step C the computer processor 1 will execute processing step Q4 to determine if the last outpatient billing record has been read. When all of the outpatient billing records contained in the processed medical billing record storage medium 4 have been compared to the initial inpatient billing record highlighted in processing step A the computer processor 1 will execute processing step Q5 to determine if the last inpatient billing record has been highlighted. If not the computer processor 1 will execute processing step E to read and highlight the next inpatient billing record from the processed medical billing record storage medium 4 for comparison with the entire set of output billing records, beginning with the initial outpatient billing record which is again read in re-executed processing step B.

For each inpatient billing record highlighted in processing step E the computer processor 1 will repeat the loop formed by processing steps C, Q1, and Q4 for each non-matching set of billing records to ensure that each inpatient billing record has been compared to each outpatient billing record. The computer processor 1 exits the processing sequence in processing step F after each inpatient billing record has been compared to each outpatient billing record contained in the processed medical billing record storage medium 4.

When a patient identification code match between inpatient and outpatient billing records has been obtained in processing step Q1 the computer processor 1 executes processing steps Q2 and Q3 to determine if the outpatient service could fall under the "72 hour billing rule" for submitting Medicare outpatient claims.

In addition to containing a patient identification code, each inpatient billing record stored in the processed medical billing record storage medium 4 contains dates of medical inpatient admission and discharge. Similarly each outpatient billing record contains a date of medical outpatient service. In processing step Q2 the computer processor 1 compares the date of medical inpatient admission from the inpatient billing record with the date of medical outpatient service from the matching outpatient billing record. If the date of outpatient service was within a preselected time period prior to the inpatient admission date, the computer processor 1 executes processing step D to combine the matching inpatient and outpatient billing records for storage in the separate "exceptions" database on the processed medical billing record storage medium 4. This preselected time period is programmed into the processing software and can be changed, but is preferably set at 72 hours for use of the software in conjunction with the Medicare "72 hour billing rule".

The computer processor 1 proceeds to processing step Q3 if the date of outpatient service from the outpatient billing record was not within the 72 hour period prior to the date of inpatient admission from the matching input billing record. In processing step Q3, the date of outpatient service is compared with both the date of inpatient admission and the date of inpatient discharge to determine if the outpatient service was performed during the inpatient stay. If the date of outpatient service was between the dates of inpatient admission and discharge the computer processor 1 again executes processing step D to combine the records for storage in the exceptions database on the processed medical billing record storage medium 4. If neither of the conditions tested in processing steps Q2 and Q3 is fulfilled the computer processor 1 proceeds to processing step Q4 and follows the processing sequence described above from that point to continue comparing inpatient and outpatient billing records.

The end result of the operations described above is that Medicare claims will be distinguished for future examination and possible reimbursement for outpatient service performed on a given patient that fell within the 72 hour period prior to that patient's inpatient admission as well as for outpatient service performed during the inpatient stay. The determination of whether reimbursement must be made for the distinguished outpatient claims will turn on whether the outpatient claim was "medically related" to the inpatient stay in accordance with Medicare billing policies. This determination can be performed manually by claims processing personnel or it can be performed automatically by the medical billing record processing software. The processing software contains instructions for manually updating via keyboard entry the exceptions database on the processed medical billing record storage medium 4 to indicate whether the matching inpatient and outpatient claims are "medically related". U.S. Pat. No. 5,253,164, which is incorporated by reference herein, discloses an example of how the "medically related" determination can be performed automatically by the processing software.

The medical billing record processing software also contains instructions for updating the exceptions database to indicate refund amounts and whether the refund was made to the payor of coinsurance or the payor of a deductible premium on a coinsurance policy supplementing the Medicare coverage. The processing software can either manually or automatically update the matching billing records to provide refund information. An example of how this update can be performed automatically by the processing software is disclosed in U.S. Pat. No. 5,253,164. These updates can be displayed along with all other information from the applicable exceptions database entry by use of the output display device 5.

The medical billing information processing software contains a final set of instructions for generating and storing chronological information to uniquely identify each user of the software and the corresponding time of use for auditing purposes. This information can be stored in the exceptions database on the processed medical billing record storage medium 4 and can also be displayed by use of the output display device 5.

An alternative embodiment of the medical billing record processing software can function in accordance with the flow diagram shown in FIG. (3). This alternative embodiment of the software is designed to automatically screen pre-existing medical billing record information to identify patients transferred between medical service providers during treatment of the same or related medical problems.

As described for the preferred embodiment, the computer processor 1 first imports all Medicare Remittance Advice (RA) billing record data onto the processed medical billing record storage medium 4 from a pre-existing database on the input medical billing record storage medium 3 while converting the RA data into a format suitable for use by the processing software.

The billing record processing instructions are then loaded from the instruction set storage medium 2 into the computer processor 1 for execution. In the first step AA of the processing sequence the computer processor 1 reads and highlights the initial medical inpatient billing record contained in the processed medical billing record storage medium 4 for comparison with the next medical inpatient billing record retrieved from the processed medical billing record storage medium 4 in processing step BB.

As described above for the preferred embodiment, each inpatient medical billing record stored in the processed medical billing record storage medium 4 contains a patient identification code unique to a single billed medical patient. In processing step QQ1 the computer processor 1 compares the patient identification codes from the inpatient billing records retrieved in processing steps AA and BB to determine whether a match exists. If not the computer processor 1 re-executes processing step BB to examine the next inpatient billing record from the processed medical billing record storage medium 4, followed by processing step QQ1 to compare the patient identification code from the new inpatient billing record to the initial inpatient billing record highlighted in processing step AA.

The computer processor 1 will repeat processing steps BB and QQ1 for each inpatient billing record retrieved in processing step BB that does not match the patient identification code contained in the initial inpatient billing record highlighted in processing step AA. Prior to each repeat of processing step BB the computer processor 1 will execute processing step QQ2 to determine if the last inpatient billing record has been read. When all of the inpatient billing records contained in the processed medical billing record storage medium 4 have been compared to the initial inpatient billing record highlighted in processing step AA, the computer processor 1 will execute processing step QQ4 to determine if the last inpatient billing record has been highlighted. If not the computer processor 1 will execute processing step DD to read and highlight the next inpatient billing record from the processed medical billing record storage medium 4 for comparison with the entire set of input billing records less those already highlighted, beginning with the next inpatient billing record which is read in re-executed processing step BB.

For each inpatient billing record highlighted in processing step DD the computer processor 1 will repeat the loop formed by processing steps BB, QQ1, and QQ2 for each non-matching set of billing records to ensure that each inpatient billing record has been compared to all other inpatient billing records. The computer processor 1 exits the processing sequence in processing step EE after each inpatient billing record has been compared to all other inpatient billing records contained in the processed medical billing record storage medium 4.

When a patient identification code match between a pair of inpatient billing records has been obtained in processing step QQ1, the computer processor 1 executes processing step QQ3 to determine if the admission date from one inpatient billing record matches the discharge date from the other inpatient billing record in the matching pair. If a match between admission and discharge dates is found the computer processor 1 executes processing step CC to combine the matching pair of inpatient billing records for storage in the separate "exceptions" database on the processed medical billing record storage medium 4. If the condition tested in processing step QQ3 is not fulfilled, the computer processor 1 proceeds to processing step QQ2 and follows the processing sequence described above from that point to continue comparing inpatient billing records.

The end result of the operations described for the alternative embodiment is that Medicare claims will be distinguished for future examination and possible reimbursement for inpatient admissions that fell on the same date as an inpatient discharge from another medical treatment provider facility. As in the preferred embodiment, the determination of whether reimbursement must be made for the distinguished claims will turn on whether the claims were "medically related" to the inpatient stay in accordance with Medicare billing policies. As in the preferred embodiment, this determination can be performed manually by claims processing personnel or it can be performed automatically by the medical billing record processing software in accordance with the method disclosed in U.S. Pat. No. 5,253,164.

As in the preferred embodiment, the alternate embodiment of the medical billing record processing software contains instructions for updating the exceptions database to indicate refund amounts and whether the refund was made to the payor of coinsurance or the payor of a deductible premium on a coinsurance policy supplementing the Medicare coverage. As in the preferred embodiment the processing software can either manually or automatically update the matching billing records to provide the refund information. As described above, an example of how this update could be performed automatically by the processing software is disclosed in U.S. Pat. No. 5,253,164. As in the preferred embodiment, these updates can be displayed along with all other information from the applicable exceptions database entry by use of the output display device 5.

Finally as in the preferred embodiment, the alternate embodiment of the medical billing information processing software contains a set of instructions for generating and storing chronological information uniquely identifying each user of the software and the corresponding time of use for auditing purposes. As in the preferred embodiment, this information can be stored in the exceptions database on the processed medical billing record storage medium 4 and can also be displayed by use of the output display device 5.

While presently preferred embodiments have been shown and described with particularity, it is to be understood that the invention may be otherwise embodied within the scope of the appended claims.

What is claimed is:

1. At least one set of computer-coded instructions stored on at least one first computer-readable storage medium for directing at least one computer processor to perform information processing on medical billing record information, comprising:
   A. at least one set of instructions for receiving information from a plurality of input medical billing records wherein said input billing records are stored on at least one second computer-readable storage medium coded in a convertible form suitable for said processing wherein:
      (i) each said input billing record contains a patient identification code unique to a single billed medical patient; and
      (ii) each said input billing record contains either dates of medical inpatient admission and discharge or a date of medical outpatient service for said patient;
   B. at least one set of instructions for processing information from said input medical billing records wherein:
      (i) each said input billing record with dates of medical inpatient admission and discharge is compared to each said input billing record with a date of medical outpatient service to determine whether said patient identification codes match;
      (ii) said input billing records with matching patient identification codes are further compared wherein:
         (a) said matching billing records are distinguished if said outpatient service date is within a preselected time period prior to said inpatient admission date; or
         (b) said matching billing records are distinguished if said outpatient service date falls between said inpatient admission date and said inpatient discharge date;
   C. at least one set of instructions for storing converted information from said input medical billing records on at least one third computer-readable storage medium having a plurality of databases wherein:
      (i) said input billing records containing dates of medical inpatient admission and discharge are stored in a first database;
      (ii) said input billing records containing dates of medical outpatient service are stored in a second database; and
      (iii) said distinguished matching billing records are combined for storage in a third database.

2. The computer-coded instructions of claim 1, further comprising:
   at least one set of instructions for updating said stored distinguished matching billing record information wherein:
      (i) said distinguished matching billing records are updated to indicate whether said medical inpatient admission was medically related to said medical outpatient service; and
      (ii) said distinguished matching billing records are updated to indicate whether a refund was generated for said medically related service.

3. The computer-coded instructions of claim 1, wherein said preselected time period is 72 hours.

4. The computer-coded instructions of claim 2, wherein said preselected time period is 72 hours.

5. The computer-coded instructions of claim 1, wherein said preselected time period is 96 hours.

6. The computer-coded instructions of claim 2, wherein said preselected time period is 96 hours.

7. The computer-coded instructions of claim 1, further comprising at least one set of instructions for comparing said distinguished matching billing records to determine whether said medical inpatient admission was medically related to said medical outpatient service.

8. The computer-coded instructions of claim 2, further comprising at least one set of instructions for comparing said distinguished matching billing records to determine whether said medical inpatient admission was medically related to said medical outpatient service.

9. The computer-coded instructions of claim 7, further comprising at least one set of instructions for generating a refund for said medically related service.

10. The computer-coded instructions of claim 8, further comprising at least one set of instructions for generating a refund for said medically related service.

11. The computer-coded instructions of claim 9, wherein said instructions for generating a refund for said medically related service determine the amount of said refund and the payee of said refund.

12. The computer-coded instructions of claim 10, wherein said instructions for generating a refund for said medically related service determine the amount of said refund and the payee of said refund.

13. The computer-coded instructions of claim 11, wherein said payee is selected from the group consisting of payors of coinsurance and deductible premiums.

14. The computer-coded instructions of claim 12, wherein said payee is selected from the group consisting of payors of coinsurance and deductible premiums.

15. The computer-coded instructions of claim 1, further comprising at least one set of instructions for displaying information contained in said stored medical billing records wherein:
   (i) said stored information is convertible into a form suitable for visual display; or
   (ii) said stored information is convertible into a form suitable for printed display.

16. The computer-coded instructions of claim 1, further comprising at least one set of instructions for storing on at least one computer-readable storage medium chronological information uniquely identifying each user and corresponding time of use of said computer-coded instructions wherein:
   (i) said chronological information is convertible into a form suitable for visual display; or
   (ii) said chronological information is convertible into a form suitable for printed display.

17. At least one set of computer-coded instructions stored on at least one first computer-readable storage medium for directing at least one computer processor to perform information processing on medical billing record information, comprising:
   A. at least one set of instructions for receiving information from a plurality of input medical billing records wherein said input billing records are stored on at least one second computer-readable storage medium coded in a convertible form suitable for said processing wherein:
      (i) each said input billing record contains a patient identification code unique to a single billed medical patient; and
      (ii) each said input billing record contains dates of medical inpatient admission and discharge for said patient;
   B. at least one set of instructions for processing information from said input medical billing records wherein:
      (i) each said input billing record is paired with each other said input billing record to determine whether said patient identification codes match;
      (ii) said pairs of input billing records with matching patient identification codes are further compared wherein said pair is distinguished if said inpatient admission date from one said billing record in said pair matches said inpatient discharge date from the other said billing record in said pair;
   C. at least one set of instructions for storing converted information from said input medical billing records on at least one third computer-readable storage medium having a plurality of databases wherein:
      (i) said input billing records are stored in a first database; and
      (iii) said distinguished matching billing record pairs are stored in a second database.

18. The computer-coded instructions of claim 17, further comprising:
   at least one set of instructions for updating said stored distinguished matching billing record information wherein:
      (i) said distinguished matching billing record pairs are updated to indicate whether said medical inpatient admissions were medically related; and
      (ii) said distinguished matching billing record pairs are updated to indicate whether a refund was generated for said medically related admissions.

19. The computer-coded instructions of claim 17, further comprising at least one set of instructions for comparing said distinguished matching billing records to determine whether said medical inpatient admissions were medically related.

20. The computer-coded instructions of claim 18, further comprising at least one set of instructions for comparing said distinguished matching billing records to determine whether said medical inpatient admissions were medically related.

21. The computer-coded instructions of claim 19, further comprising at least one set of instructions for generating a refund for said medically related admissions.

22. The computer-coded instructions of claim 20, further comprising at least one set of instructions for generating a refund for said medically related admissions.

23. The computer-coded instructions of claim 21, wherein said instructions for generating a refund for said medically related admissions determine the amount of said refund and the payee of said refund.

24. The computer-coded instructions of claim 22, wherein said instructions for generating a refund for said medically related admissions determine the amount of said refund and the payee of said refund.

25. The set of computer-coded instructions of claim 23, wherein said payee is selected from the group consisting of payors of coinsurance and deductible premiums.

26. The set of computer-coded instructions of claim 24, wherein said payee is selected from the group consisting of payors of coinsurance and deductible premiums.

27. The computer-coded instructions of claim 17, further comprising at least one set of instructions for displaying information contained in said stored medical billing records wherein:
   (i) said stored information is convertible into a form suitable for visual display; or
   (ii) said stored information is convertible into a form suitable for printed display.

28. The computer-coded instructions of claim 17, further comprising at least one set of instructions for storing on at least one computer-readable storage medium chronological information uniquely identifying each user and corresponding time of use of said computer-coded instructions wherein:
   (i) said chronological information is convertible into a form suitable for visual display; or
   (ii) said chronological information is convertible into a form suitable for printed display.

* * * * *